(12) United States Patent
Anderson et al.

(10) Patent No.: US 11,399,914 B2
(45) Date of Patent: Aug. 2, 2022

(54) SELF-ILLUMINATING MICROSURGICAL CANNULA DEVICE

(71) Applicant: Alcon Inc., Fribourg (CH)

(72) Inventors: Joshua Anderson, Keller, TX (US); James Y. Chon, Irvine, CA (US); Mark Harrison Farley, Laguna Hills, CA (US); Paul R. Hallen, Colleyville, TX (US); Niels Alexander Abt, Winterthur (CH)

(73) Assignee: Alcon Inc., Fribourg (CH)

( * ) Notice: Subject to any disclaimer, the term of this patent is extended or adjusted under 35 U.S.C. 154(b) by 534 days.

(21) Appl. No.: 16/030,986

(22) Filed: Jul. 10, 2018

(65) Prior Publication Data

US 2019/0046288 A1    Feb. 14, 2019

Related U.S. Application Data

(60) Provisional application No. 62/542,902, filed on Aug. 9, 2017.

(51) Int. Cl.
| | |
|---|---|
| *A61B 17/34* | (2006.01) |
| *A61B 90/92* | (2016.01) |
| *A61F 9/007* | (2006.01) |
| *A61B 90/30* | (2016.01) |
| *A61B 3/00* | (2006.01) |

(Continued)

(52) U.S. Cl.
CPC .......... *A61B 90/30* (2016.02); *A61B 3/0008* (2013.01); *A61B 17/0218* (2013.01); *A61B 17/0231* (2013.01); *A61B 17/3421* (2013.01); *A61B 17/3423* (2013.01); *A61B 17/3462* (2013.01); *A61B 90/92* (2016.02); *A61F 9/007* (2013.01); *A61B 2017/00345* (2013.01); *A61B 2090/304* (2016.02)

(58) Field of Classification Search
CPC .............. A61B 90/92; A61B 2090/304; A61B 17/3421; A61B 3/0008; A61B 17/0231; A61B 17/3462; A61F 9/00727; A61F 2250/005; A61F 17/3423
See application file for complete search history.

(56) References Cited

U.S. PATENT DOCUMENTS

| | | |
|---|---|---|
| 3,764,796 A | 10/1973 | Gilliam et al. |
| 3,774,022 A | 11/1973 | Dubrow et al. |
| 3,819,925 A | 6/1974 | Richter et al. |

(Continued)

FOREIGN PATENT DOCUMENTS

| | | |
|---|---|---|
| CN | 107174398 A | 9/2017 |
| EP | 1772110 A1 | 4/2007 |

(Continued)

OTHER PUBLICATIONS

Alcon Global Vitreoretinal Product Catalog, Feb. 2014 (59 pages).
Luminox Press Release, 2009 (2 pages).

*Primary Examiner* — David W Bates (57) ABSTRACT

Provided herein are cannula devices that are self-illuminating to facilitate visualization of the cannula devices during a surgical procedure. The self-illuminating feature may be provided by phosphors incorporated into the cannula device, for example in the hub or sealing element of the cannula device. The cannula device may emit light of a specific color selected to correspond to a size of the cannula device.

14 Claims, 5 Drawing Sheets

(51) Int. Cl.
  *A61B 17/02* (2006.01)
  *A61B 17/00* (2006.01)

(56) References Cited

U.S. PATENT DOCUMENTS

| | | | |
|---|---|---|---|
| 3,933,118 A | 1/1976 | Lyons et al. | |
| 4,064,428 A | 12/1977 | Van Zandt | |
| 5,179,938 A * | 1/1993 | Lonky | A61B 1/31 600/222 |
| 5,201,730 A | 4/1993 | Easley | |
| 5,263,944 A * | 11/1993 | Vidal | A61B 17/3462 604/167.01 |
| 5,275,593 A | 1/1994 | Easley et al. | |
| 5,329,938 A | 7/1994 | Lonky | |
| 5,556,417 A * | 9/1996 | Sher | A61B 17/0231 600/236 |
| 5,591,160 A | 1/1997 | Reynard | |
| 5,651,783 A | 7/1997 | Raynard | |
| 5,819,727 A | 10/1998 | Linder | |
| 5,931,383 A * | 8/1999 | Palmer | A47G 21/182 239/33 |
| 6,189,533 B1 * | 2/2001 | Simon | A61B 1/267 128/200.26 |
| 6,797,521 B2 | 9/2004 | Grissom | |
| 7,527,387 B2 | 5/2009 | Birkenbach | |
| 7,783,346 B2 | 8/2010 | Smith et al. | |
| 7,784,946 B2 | 8/2010 | Leblanc | |
| 8,343,106 B2 | 1/2013 | Lopez et al. | |
| 8,371,695 B2 | 2/2013 | Papac et al. | |
| 8,398,236 B2 | 3/2013 | Juhasz | |
| 8,679,064 B2 * | 3/2014 | Lopez | A61F 9/007 604/165.04 |
| 8,968,347 B2 | 3/2015 | McCollam | |
| 9,055,885 B2 | 6/2015 | Horvath | |
| 9,089,364 B2 | 7/2015 | Bhadri | |
| 9,119,565 B2 | 9/2015 | Levis | |
| 9,351,758 B2 | 5/2016 | Baldwin | |
| 9,364,982 B2 | 6/2016 | Schaller | |
| 9,402,643 B2 | 8/2016 | Auld | |
| 9,561,085 B2 | 2/2017 | Yadlowsky | |
| 9,839,749 B2 | 12/2017 | Johnson | |
| 9,956,053 B2 | 5/2018 | Diao | |
| 10,016,248 B2 | 7/2018 | Mirsepassi | |
| 10,039,669 B2 | 8/2018 | Heeren | |
| 10,244,931 B2 | 4/2019 | Kern | |
| 10,307,290 B2 | 6/2019 | Kern | |
| 10,376,414 B2 | 8/2019 | Hallen | |
| 2005/0065496 A1 * | 3/2005 | Simon | A61B 90/36 604/500 |
| 2005/0096698 A1 * | 5/2005 | Lederman | A61B 90/92 606/222 |
| 2005/0099824 A1 * | 5/2005 | Dowling | A61B 1/0653 362/572 |
| 2005/0222617 A1 * | 10/2005 | Ororz | A61B 90/92 606/223 |
| 2006/0085005 A1 * | 4/2006 | Kenealy, III | A61C 8/0089 606/80 |
| 2008/0215078 A1 | 9/2008 | Bennett | |
| 2008/0319432 A1 * | 12/2008 | Ely | A61B 90/94 606/14 |
| 2009/0054957 A1 * | 2/2009 | Shanbaky | A61B 3/0008 607/89 |
| 2009/0114701 A1 * | 5/2009 | Zemlok | A61B 17/064 227/176.1 |
| 2009/0124960 A1 | 5/2009 | Mackool | |
| 2009/0161384 A1 | 6/2009 | Smith | |
| 2010/0274093 A1 * | 10/2010 | Shelton, IV | A61B 17/3423 600/206 |
| 2011/0120459 A1 * | 5/2011 | Ramos | A61B 1/0676 128/200.26 |
| 2011/0122366 A1 | 5/2011 | Smith | |
| 2011/0282160 A1 * | 11/2011 | Bhadri | A61B 1/0684 600/236 |
| 2012/0080496 A1 | 4/2012 | Schall et al. | |
| 2013/0109925 A1 * | 5/2013 | Horton | A61B 17/56 600/235 |
| 2013/0131459 A1 * | 5/2013 | Williams | A61B 17/4241 600/249 |
| 2013/0274634 A1 * | 10/2013 | Blom | A61B 17/3468 600/593 |
| 2014/0121469 A1 | 5/2014 | Meckel | |
| 2014/0296638 A1 * | 10/2014 | Komukai | A61B 1/0653 600/121 |
| 2014/0357948 A1 * | 12/2014 | Kikuchi | A61B 1/018 600/104 |
| 2016/0038155 A1 * | 2/2016 | Griffith | A61B 17/1322 606/203 |
| 2016/0302878 A1 | 10/2016 | Kern | |
| 2017/0014023 A1 | 1/2017 | Kern | |
| 2017/0014267 A1 | 1/2017 | Kern | |
| 2017/0119491 A1 | 5/2017 | Mirsepassi | |
| 2017/0165114 A1 | 6/2017 | Hallen | |
| 2018/0055596 A1 | 3/2018 | Johnson | |
| 2018/0132963 A1 | 5/2018 | Diao | |
| 2018/0133057 A1 | 5/2018 | Diao | |
| 2018/0168768 A1 | 6/2018 | Mirsepassi | |
| 2018/0168861 A1 | 6/2018 | Mirsepassi | |
| 2018/0338776 A1 | 11/2018 | Farley | |
| 2018/0338859 A1 | 11/2018 | Mirsepassi | |
| 2018/0338860 A1 | 11/2018 | Farley | |
| 2019/0046288 A1 | 2/2019 | Anderson | |
| 2019/0076211 A1 * | 3/2019 | Palushi | A61M 25/0105 |
| 2019/0159662 A1 * | 5/2019 | Papas | A61B 1/07 |
| 2019/0183680 A1 | 6/2019 | Abt | |
| 2019/0210206 A1 * | 7/2019 | Nix | B25F 1/003 |
| 2019/0239979 A1 * | 8/2019 | Abt | A61B 17/3421 |
| 2019/0307527 A1 | 10/2019 | Grueebler | |
| 2020/0022773 A1 | 1/2020 | Grueebler | |

FOREIGN PATENT DOCUMENTS

| | | |
|---|---|---|
| EP | 2243436 A2 | 10/2010 |
| WO | 03075979 A2 | 9/2003 |
| WO | WO2015087091 A1 | 6/2015 |

* cited by examiner

SELF-ILLUMINATING MICROSURGICAL CANNULA DEVICE

This application claims the benefit of priority of U.S. Provisional Patent Application Ser. No. 62/542,902 titled "Self-Illuminating Microsurgical Cannula Device", filed on Aug. 9, 2017, whose inventors are Joshua Anderson, James Y. Chon, Mark Harrison Farley and Paul R. Hallen, which is hereby incorporated by reference in its entirety as though fully and completely set forth herein.

TECHNICAL FIELD

The present disclosure is directed to cannulas for facilitating insertion of instruments during microsurgical procedures and related methods of use.

BACKGROUND

A number of different types of ophthalmic medical conditions can be treated with microsurgical procedures that involve the insertion of microsurgical instruments into the human eye. For example, vitreo-retinal procedures may be performed to treat conditions such as age-related macular degeneration (AMD), diabetic retinopathy, diabetic vitreous hemorrhage, macular hole, retinal detachment, epiretinal membrane, cytomegalovirus (CMV) retinitis, and many other ophthalmic conditions. Vitrectomy procedures involve removing all or part of the vitreous humor from the eye. In such vitreo-retinal procedures, instruments are typically inserted into the eye through the pars plana into the posterior chamber of the eye. Other ophthalmic microsurgical procedures may involve insertion of instruments into the eye at other locations.

With respect to posterior segment surgery, the instruments that may be used include, for example, a vitreous cutter probe, a laser probe, or an ultrasonic fragmenter for cutting or fragmenting the tissue. Each instrument may be connected to a control console by a long air-pressure (pneumatic) line and/or power cable, optical cable, or flexible tubes for supplying an infusion fluid to the surgical site or for withdrawing or aspirating fluid and cut/fragmented tissue from the site. The cutting, infusion, and aspiration functions of the instruments may be controlled by the console that not only provides power for the surgical instruments (e.g., a reciprocating or rotating cutting blade or an ultrasonically vibrated needle), but may also control the flow of infusion fluid and provide a source of vacuum (relative to atmosphere) for the aspiration of fluid and cut/fragmented tissue. The functions of the console may be controlled manually by the surgeon, e.g., through use of a foot-operated switch or proportional control.

In ophthalmic microsurgical procedures, a surgeon may be required to insert and withdraw an instrument multiple times, or to insert and withdraw multiple instruments. If the instruments directly contact an incision site, the insertion, manipulation, and withdrawal of the instruments can cause trauma to the eye. In order to minimize the need for making multiple incisions, to provide simple insertion and withdrawal of instruments, to reduce the chance for trauma at the incision site, and to promote healing, a surgeon may insert one or more cannulas into the eye, each cannula serving as an entryway or entry port for instruments into the eye. A typical cannula is a small tube with an attached hub. The tube is inserted into the eye, and the hub acts as a stop limiting the advancement of the tube into the eye and preventing the tube from completely entering the eye. The hub may be stitched to the eye to keep the cannula in place. The cannula allows the surgeon to insert one or more microsurgical instruments through the tube into the eye. Examples of cannulas are disclosed in U.S. Pat. Nos. 8,343,106 and 8,679,064, the disclosures of which are hereby incorporated by reference herein.

It is typically desirable to use the smallest size cannula suitable for the instruments to be used, in order to minimize the size of the incision into the eye. Depending on the size of the incision, the incision may be small enough to render a resulting wound substantially self-healing, thereby eliminating the need to employ additional procedures to close the incision, such as sutures.

Multiple cannulas may be inserted when, for example, it is desired to use multiple instruments simultaneously. In some instances, it may be desirable to use cannulas of different sizes simultaneously, for example when it is desired to use instruments of different sizes simultaneously.

To aid it identifying which instruments go with which cannula, the cannulas have in the past been color-coded, with the color indicating the size associated with the cannula. For example, a 23 gauge cannula may have a hub with a first color (e.g., orange), a 25 gauge cannula may have a hub with a second color (e.g., blue or teal), and a 27 gauge cannula may have a hub with a third color (e.g., purple). In this way, after the cannulas are in place in the eye, when the surgeon desires to insert an instrument of a particular size into the eye, the surgeon can identify the sizes of the cannulas by their color in order to determine the appropriate cannula into which to insert the instrument.

SUMMARY

The present disclosure is directed to improved cannulas for facilitating insertion of instruments during microsurgical procedures.

During ophthalmic surgical procedures, room lighting is often dim. It can be difficult to see the cannulas that have been inserted into the eye, and it can be difficult to distinguish between different cannula colors. In the past, during instrument exchanges, surgeons often have needed to turn microscope illumination back on to provide sufficient visual contrast to guide instrument insertion.

In an exemplary embodiment in accordance with the present disclosure, a cannula device is provided to be self-illuminating. The self-illumination may be provided by phosphors in the cannula device, such as a phosphorescent pigment used in manufacturing the cannula device. The cannula device comprises a cannula tube and a hub and optionally a sealing element. The phosphors or phosphorescent pigment may be provided in one or more of the hub, tube, or sealing element. The phosphors or phosphorescent pigment may correspond to a color-coding of the cannula device associated with a size of the cannula tube.

In an exemplary method, a first cannula device is provided with a self-illuminating feature such as phosphors or a phosphorescent pigment in the hub, tube, or sealing element of the first cannula device. The phosphors or phosphorescent pigment may correspond to a color-coding of the first cannula device associated with a size of the first cannula device. The first cannula device is inserted into an eye with the tube providing a passage for one or more instruments into the eye. A second cannula device may be provided with a self-illuminating feature such as phosphors or a phosphorescent pigment in the hub, tube, or sealing element of the second cannula device. The phosphors or a phosphorescent pigment may correspond to a color-coding of the second cannula device associated with a size of the second cannula device, wherein the size of the tube of the second cannula device is different from the size of the tube of the first cannula device, and the color of the second cannula device is different from the color of the first cannula device. The second cannula device is inserted into an eye with the tube providing a passage for one or more instruments into the eye.

The foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the accompanying drawings and the following detailed description.

BRIEF DESCRIPTION OF THE DRAWINGS

The accompanying drawings illustrate implementations of the devices and methods disclosed herein and, together with the description, serve to explain the principles of the present disclosure.

The accompanying drawings may be better understood by reference to the following detailed description.

DETAILED DESCRIPTION

For the purposes of promoting an understanding of the principles of the present disclosure, reference will now be made to the implementations illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one implementation may be combined with the features, components, and/or steps described with respect to other implementations of the present disclosure. For simplicity, in some instances the same reference numbers are used throughout the drawings to refer to the same or like parts.

Figure 1:
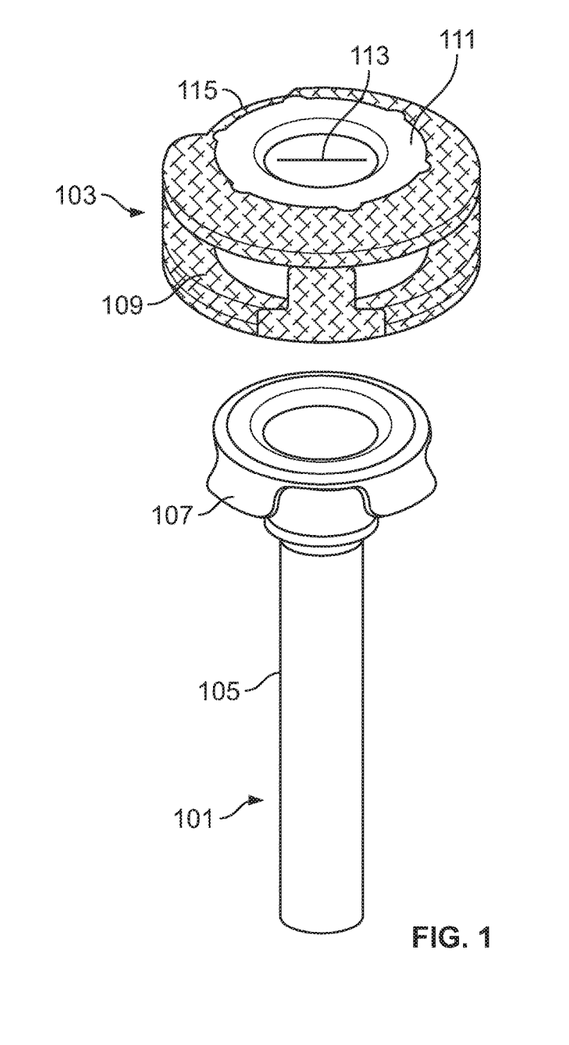
FIG. 1 illustrates a cannula tube and a self-illuminating, color-coded overcap or hub, according to an embodiment.

FIG. 1 illustrates an embodiment of a trocar cannula 101 and an overcap or hub 103. The cannula 101 may be configured for insertion into an eye to facilitate insertion and removal of instruments during surgery. The cannula 101 may include a tube or shaft 105 capable of extending into the eye (e.g., through a sclera, conjunctiva, etc). In some embodiments, the cannula 101 may be manufactured separately from the hub 103 and then attached to the hub 103. For example, the cannula 101 may include one or more tabs 107 configured to engage corresponding slots 109 in the hub 103 (e.g., the cannula 101 illustrated in FIG. 1 includes four tabs 107 to engage four corresponding slots 109 in the hub 103). Other attachments are also contemplated. For example, the cannula 101 may include the slots, and the hub 103 may include the tabs. In some embodiments, the cannula 101 may be attached to the hub 103 through adhesive, thermal bonding, etc. In other embodiments, the cannula 101 may be manufactured in one piece with the hub 103.

In some embodiments, a sealing element 111 may be coupled to the hub 103 or may otherwise be arranged to selectively seal off the passage through the cannula 101 (e.g., the sealing element 111 may be disposed at least partially between the shaft 105 and the hub 109). The sealing element 111 may be made of an elastomer (e.g., silicone). As shown in FIG. 1, a surface of the sealing element 111 may be exposed on the hub 103. In some embodiments, the exposed surface of the sealing element 111 may include one or more slits 113 to allow passage of surgical tools or instruments into the cannula 101. In a relaxed condition of the sealing element 111, i.e., in the absence of a surgical instrument (or vent or other element), the slit 113 of the sealing element 111 is closed to inhibit fluid flow through the sealing element 111 and thereby to seal off fluid passage through the cannula 101. A surgical instrument (or vent or other element) may be passed through the slit 113.

In some embodiments, the sealing element 111 may be attached to the hub 103 to inhibit rotation of the sealing element 111 relative to the hub 103. For example, the sealing element 111 may be overmolded into a depression and one or more holes in the hub 103. In some embodiments, the sealing element 111 may include a silicon wafer that is formed separately from the hub 103 and inserted between the hub 103 and the cannula 101 during assembly of the hub 103 onto the cannula 101. In such a case, the sealing element 111 may be attached to the hub 103 and cannula 101 through a friction fit. Other attachments are also contemplated (e.g., adhesive).

Figure 2A:
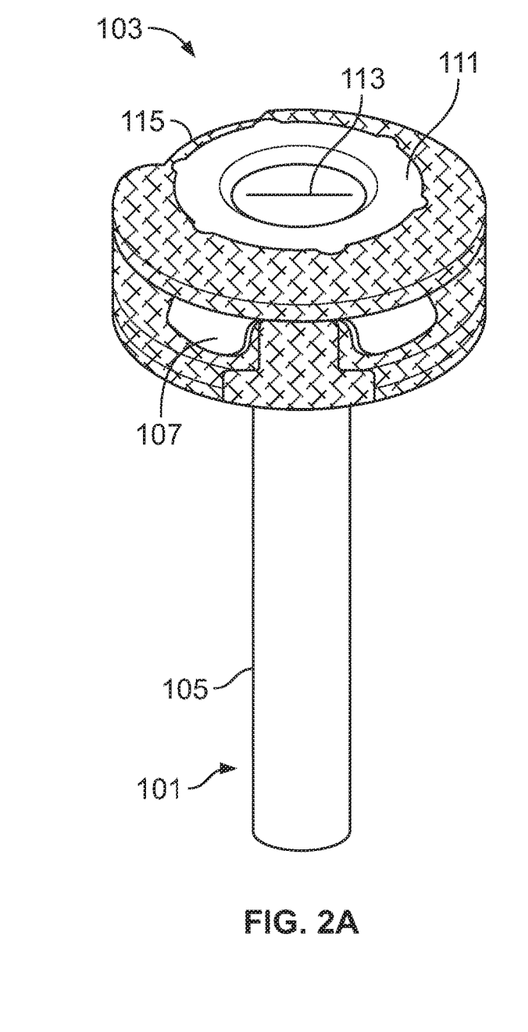
FIG. 2A illustrates a cannula device comprising the cannula tube and hub of FIG. 1 assembled together.

FIG. 2A illustrates an embodiment of an entry port or cannula device comprising the cannula 101 affixed to the hub 103 (e.g., after engagement of the tabs 107 in respective slots 109). In some embodiments, the tab/slot interface may prevent rotation of the hub 103 relative to the cannula 101 (e.g., during insertion of the cannula 101 into the eye). In some embodiments, the tabs 107 may be configured to permanently hold the hub 103 to the cannula 101 (such that the hub 103 may not be removed from the cannula 101 without destroying part of the cannula 101 and/or hub 103). For example, the tabs 107 (and cannula 101) may be made of stainless steel, and the hub 103 may be made of plastic (e.g., polycarbonate). Other materials are also contemplated. The permanent hold between the hub 103 and the cannula 101 may prevent inadvertent removal of the hub 103 from the cannula 101 during surgery (e.g., vitreoretinal surgery).

As can be seen in FIG. 2A, cannula devices as shown in FIG. 2A and as otherwise disclosed herein in accordance with other embodiments comprise a small tube with a hub at the proximal end of the tube. The tube is inserted into the eye, and the hub acts as a stop limiting the advancement of the tube into the eye and preventing the tube from completely entering the eye. The hub may be stitched to the eye to keep the cannula in place.

Cannula devices as shown in FIG. 2A and as otherwise disclosed herein in accordance with other embodiments may be provided in different sizes, having different sizes of tubes for accommodating instruments of different sizes. Examples of cannula sizes suitable for ophthalmic surgical procedures include, for example, 20 gauge, 23 gauge, 25 gauge, 27 gauge, and others. The cannula 101 in FIG. 2A may be, for example, a 23 gauge cannula.

To aid it identifying the size of the cannula, and to assist in determining which instruments go with which cannula, the cannula device may be color-coded, with the color indicating the size associated with the cannula. For example, a 23 gauge cannula may have a first color, a 25 gauge cannula may have a second color, and a 27 gauge cannula may have a third color. The color-coding may be on any visible part of the cannula device, including the hub, sealing element, and/or tube. With the color-coding, after the cannulas are in place in the eye, the surgeon can identify the cannula sizes by their color in order to determine the appropriate cannula into which to insert an instrument.

With prior devices, with dim lighting in the room of the surgical procedure, it can be difficult for the surgeon to see the cannula devices and/or their color. This may necessitate turning on a microscope light or other light for the surgeon to see the cannula devices for instrument exchanges, which can be undesirable. For example, it may cause the surgeon's eyes to have to adjust to the brighter light and then readjust when the microscope light or other light is turned off, taking time during the procedure.

In accordance with exemplary embodiments herein described, the cannula device may be self-illuminating (e.g., at least partially made of a self-illuminating material). The self-illuminating material may be a material that, for example, contains a phosphorescent pigment. The self-illumination can help the surgeon see the location of the cannula device and can help the surgeon see any color coding and thereby identify the size of the cannula device.

In the exemplary embodiment of FIG. 2A, the hub 103 may be self-illuminating, for example by being phosphorescent. The pigment used for color-coding of the hub 103 may be a phosphorescent pigment. The cannula device of FIG. 2A is color-coded with a first color (e.g., orange) to indicate the size of the cannula, e.g., 23 gauge.

Figure 2B:
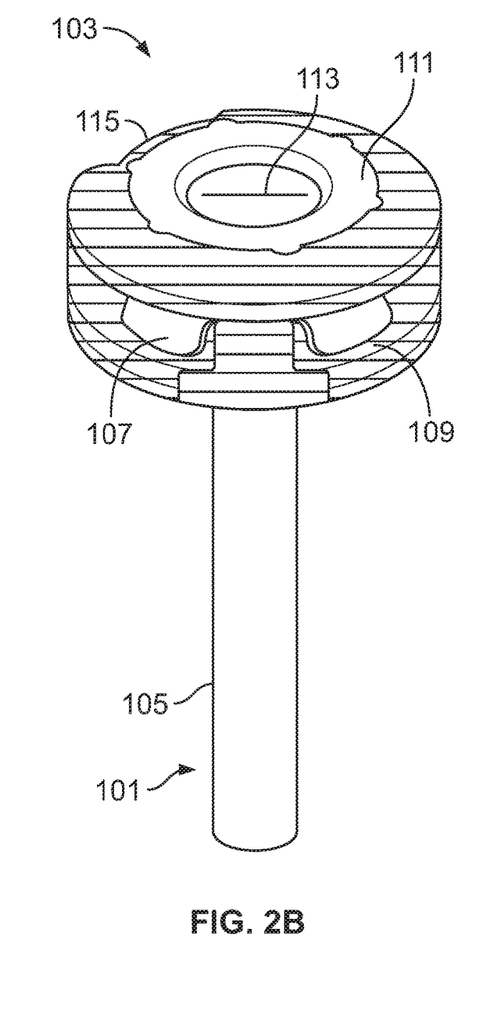
FIG. 2B illustrates a cannula device similar to the cannula device in FIG. 2A but with a different size cannula tube and different color coding.

FIG. 2B illustrates a cannula device similar to the cannula device in FIG. 2A but with a different size cannula tube and different color coding. In the exemplary embodiment of FIG. 2B, the hub 103 is also self-illuminating, for example by being phosphorescent. As with FIG. 2A, the pigment used for color-coding of the hub 103 may be a phosphorescent pigment. The cannula device of FIG. 2B is color-coded with a second color (e.g., blue or teal) to indicate the size of the cannula, e.g., 25 gauge.

Figure 2C:
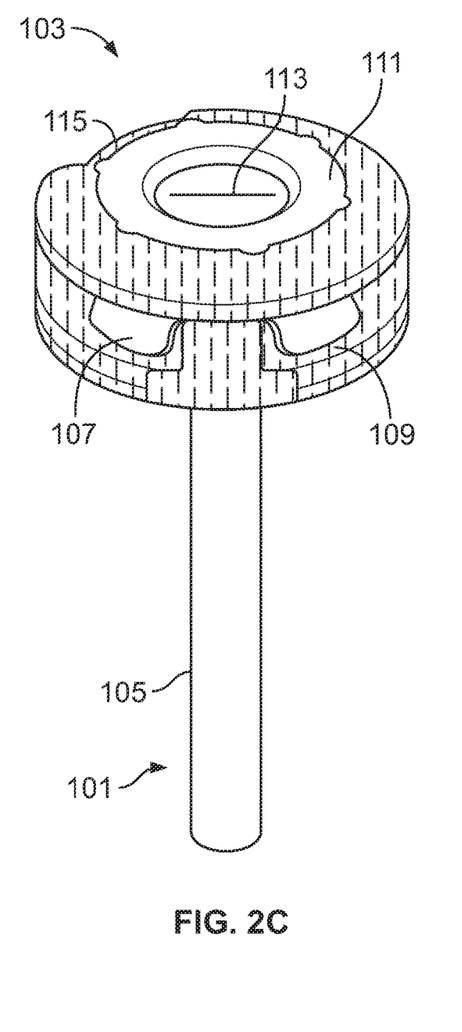
FIG. 2C illustrates a cannula device similar to the cannula devices in FIGS. 2A and 2B, but with a different size cannula tube and different color coding.

FIG. 2C illustrates a cannula device similar to the cannula devices in FIGS. 2A and 2B, but with a different size cannula tube and different color coding. In the exemplary embodiment of FIG. 2C, the hub 103 is also self-illuminating, for example by being phosphorescent. As with FIGS. 2A and 2B, the pigment used for color-coding of the hub 103 may be a phosphorescent pigment. The cannula device of FIG. 2C is color-coded with a third color (e.g., purple) to indicate the size of the cannula, e.g., 27 gauge.

Figure 3A:
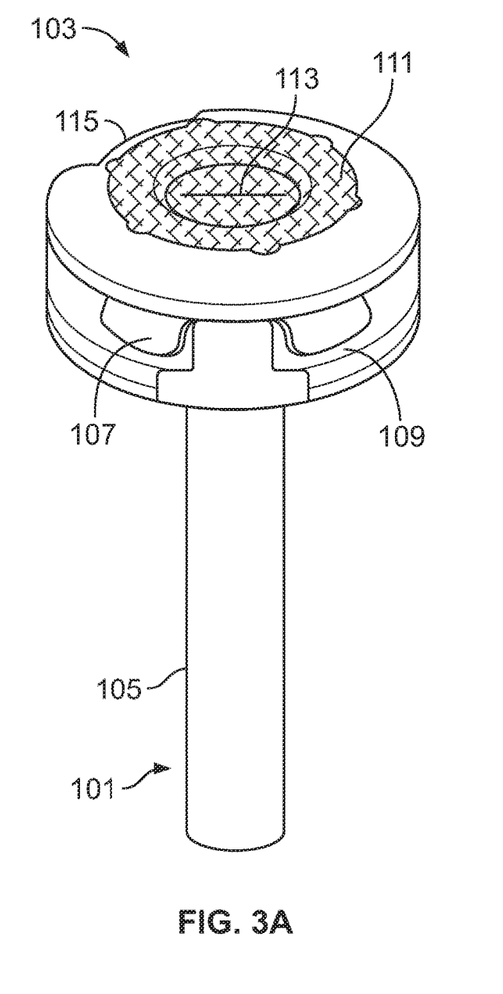
FIG. 3A illustrates a cannula device similar to the cannula device of FIG. 2A, but with the self-illuminating color coding in the elastomeric seal.
Figure 3B:
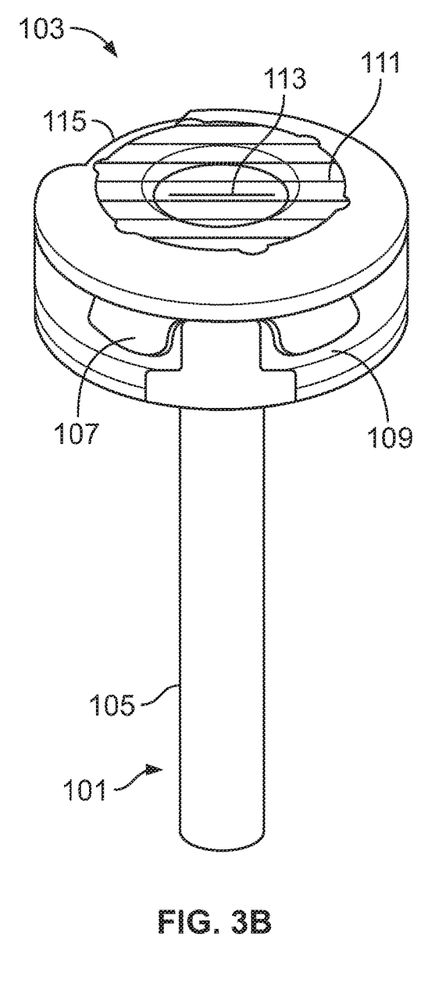
FIG. 3B illustrates a cannula device similar to the cannula device in FIG. 3A but with a different size cannula tube and different color coding.
Figure 3C:
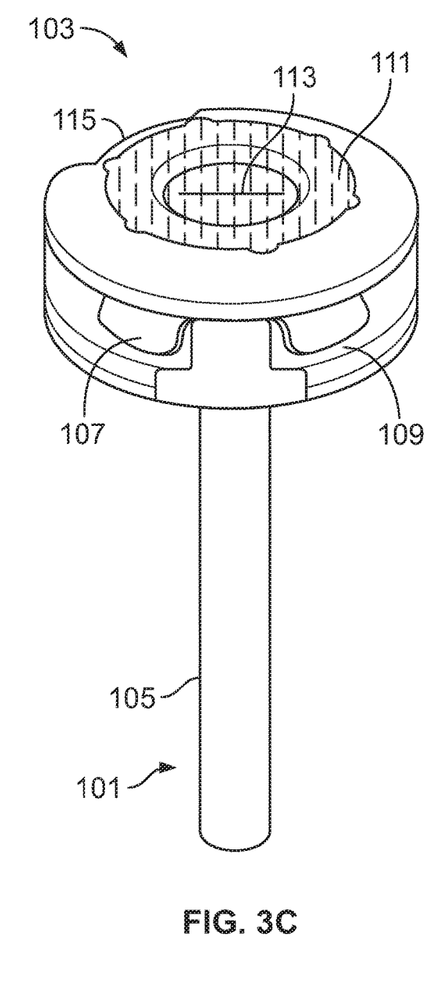
FIG. 3C illustrates a cannula device similar to the cannula devices in FIGS. 3A and 3B, but with a different size cannula tube and different color coding.

FIGS. 3A, 3B, and 3C illustrate cannula devices similar to the cannula devices of FIGS. 2A, 2B, and 2C, but with the self-illuminating color coding in the elastomeric sealing element 111. In each of FIGS. 3A, 3B, and 3C, the sealing element 111 is self-illuminating by being phosphorescent. The pigment used for color-coding of the sealing element 111 may be a phosphorescent pigment. The cannula device of FIG. 3A is color-coded with a first color (e.g., orange) to indicate the size of the cannula, e.g., 23 gauge. The cannula device of FIG. 3B is color-coded with a second color (e.g., blue or teal) to indicate the size of the cannula, e.g., 25 gauge. The cannula device of FIG. 2C is color-coded with a third color (e.g., purple) to indicate the size of the cannula, e.g., 27 gauge.

The self-illumination feature may be incorporated in any visible part of the cannula device, including the hub, sealing element, and/or tube. The self-illumination provides a "glow-in-the-dark" effect whereby the cannula device is visible in the dim or dark surgical procedure room. This feature can facilitate in-situ visualization of the cannula devices without active illumination, ease of instrument insertion into the cannula devices, and/or verification of color-coding of the cannula devices to verify gauge size.

In exemplary embodiments wherein the self-illumination feature is provided by all or part of the cannula device being phosphorescent, the phosphorescence may be excited to its luminous operating state under microscope illumination during normal surgical insertion of the cannula device into the eye. Alternatively, a separate light could be used to make the cannula device phosphoresce more. After activation by the microscope or otherwise, the phosphorescence of the cannula device emits a soft light, visible after the microscope illumination or other lighting is turned off. The phosphorescent light may be the gauge-specific colored light indicating the size of the cannula.

With the self-illumination feature, surgical efficiency is promoted without significant cost or complexity. The feature alleviates the need to turn on microscope illumination during the procedure in order for the surgeon to view the in-place cannula devices.

The desired portion(s) of the cannula devices may be made phosphorescent by incorporating suitable phosphors into the material used for manufacturing to make the material self-illuminating. For example, the phosphors may be mixed into the plastic used for making the hub and/or into the elastomer (e.g., silicone) used for making the sealing element. Examples of phosphors include zinc sulfide and strontium aluminate. The phosphors can be energized by normal light, such as the light from a microscope or in a room, and the resulting glow can last long enough for the duration of the surgical procedure. The phosphors absorb light when energized and release the stored energy to glow when the lights are off or dim. Phosphors can be selected to give a desired color of visible light after being activated. The use of phosphorescent pigments and/or dopants can be chosen to give the desired illumination.

Figure 4:
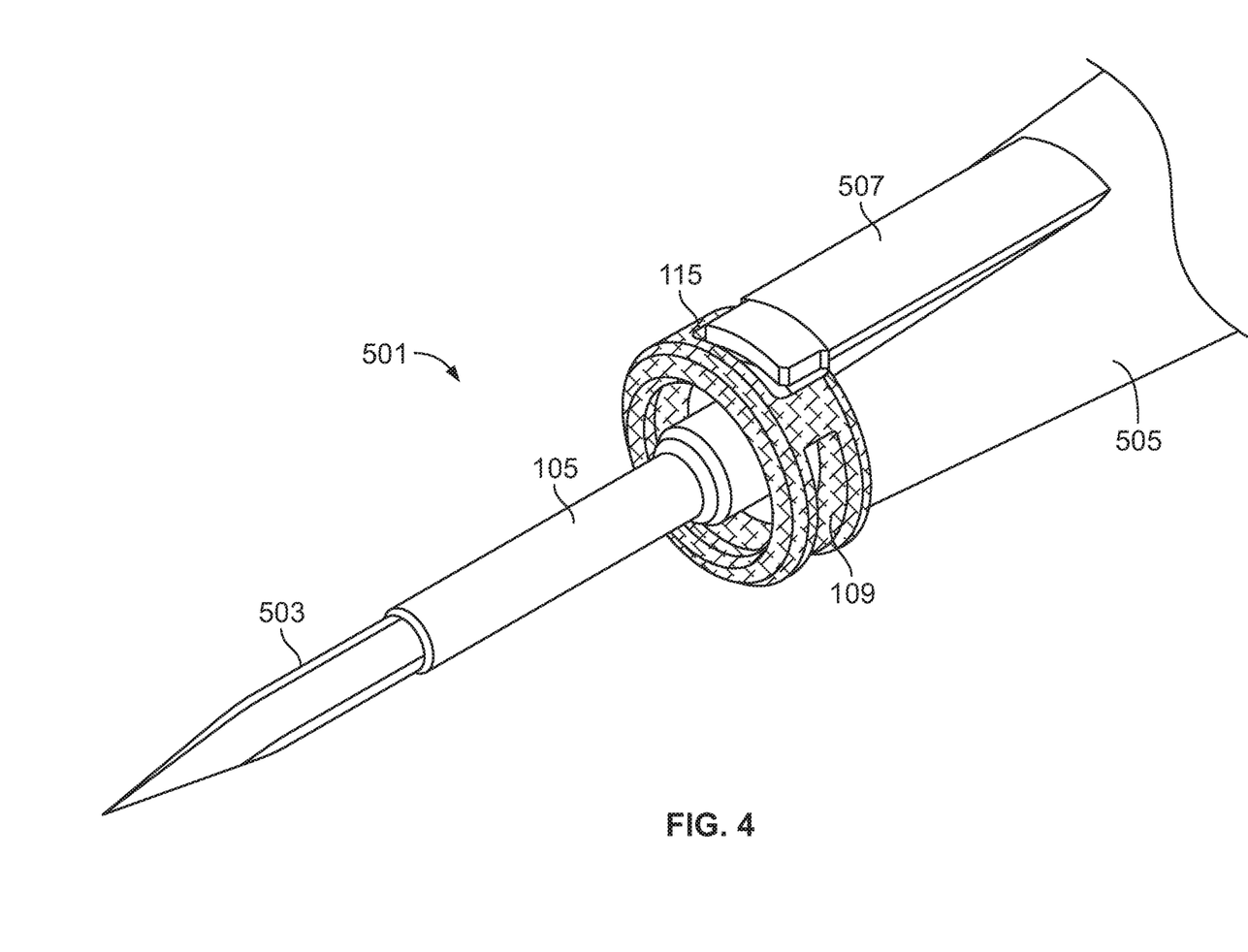
FIG. 4 illustrates the cannula device of FIG. 2A on a trocar inserter.

FIG. 4 illustrates an embodiment of a self-illuminating cannula device on a trocar inserter 501. In some embodiments, the trocar inserter 501 may include a trocar blade 503 attached to a handle 505. In some embodiments, the handle 505 may be made of plastic, and the blade 503 may be made of stainless steel. Other materials are also contemplated. The trocar blade 503 may extend past the end of the shaft 105 of the cannula device and may include one or more sharp edges to pierce an eye (e.g., pierce a hole through the sclera and into the vitreous body) for insertion of the cannula 101. In some embodiments, a guide 507 may fit into guide slot 115 of the cannula device to inhibit rotation of the cannula device relative to the handle 505 during insertion of the cannula device into eye. In some embodiments, the guide 507 may releasably engage the guide slot 115 such that when the trocar inserter 501 is withdrawn from the cannula device, the guide 507 does not pull the cannula device out of the eye. For example, the guide 507 may frictionally engage the guide slot 115 with a friction force that is less than a friction force exerted by the eye on the external sides of the cannula 101 when the cannula 101 is in the eye.

Figure 5:
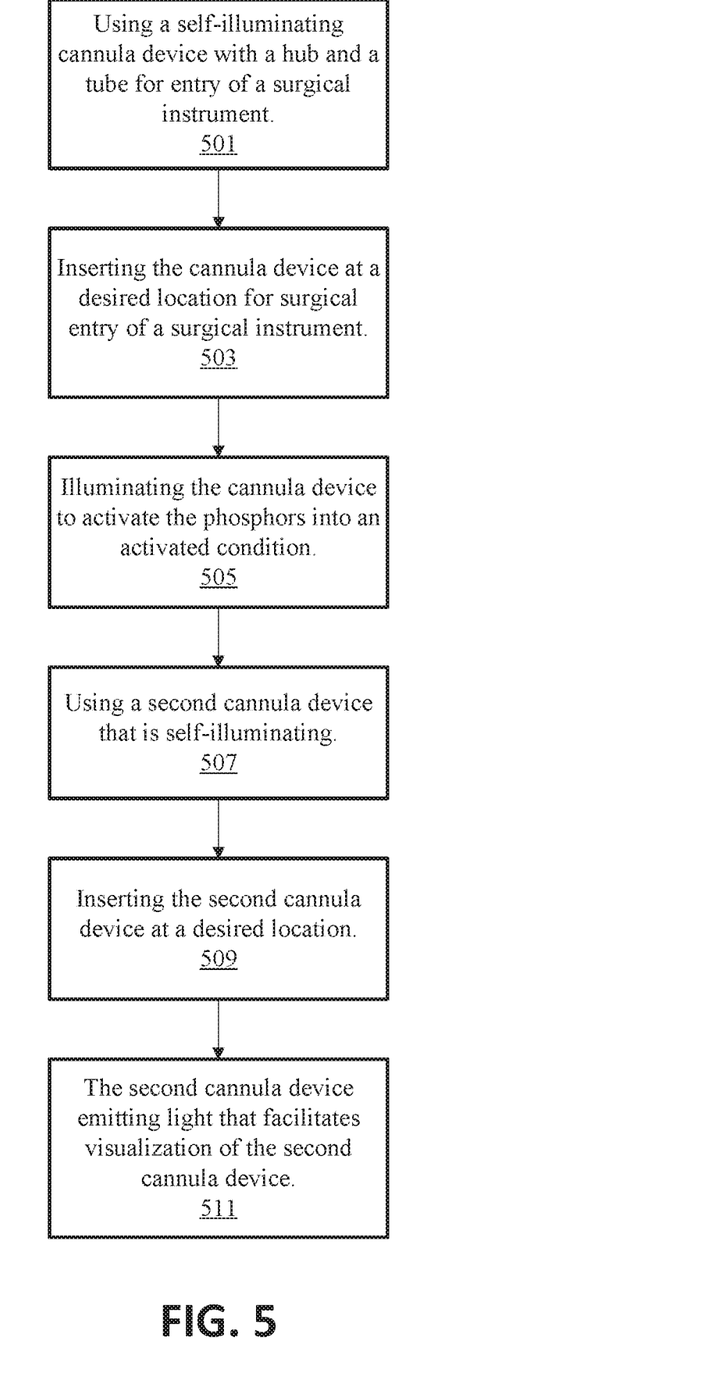
FIG. 5 illustrates a flowchart of an embodiment of a method for using a self-illuminating cannula.

FIG. 5 illustrates a flowchart of an embodiment of a method for using a self-illuminating cannula. The elements provided in the flowchart are illustrative only. Various provided elements may be omitted, additional elements may be added, and/or various elements may be performed in a different order than provided below.

At 501, a cannula device with a tube configured for entry of a surgical instrument and a hub at a proximal end of the tube may be used. The cannula device may include a self-illuminating material (e.g., phosphors) that emits light that facilitates visualization of the cannula device. For example, the hub may include a self-illuminating material. In some embodiments, the cannula device may include a sealing element configured to seal a passage through the tube when the sealing element is in a relaxed condition. In some embodiments, the sealing element may include a self-illuminating material.

At 503, the cannula device may be inserted at a desired location for surgical entry of a surgical instrument.

At 505, the cannula device may be illuminated to activate the phosphors into an activated condition. The phosphors, when in an activated condition, may emit a color-coded light corresponding to a size of the cannula device.

In some embodiments, at 507, a second cannula device may be used (where the previously mentioned cannula device is a first cannula device). The second cannula device may include a tube configured for entry of a second surgical instrument with a hub at a proximal end of the tube. The second cannula device may also be self-illuminating. In some embodiments, the first and second cannula device may be different sizes.

At 509, the second cannula device may be inserted at a desired location for surgical entry of the second surgical instrument.

At 511, after inserting the second cannula device, the second cannula device may emit light that facilitates visualization of the second cannula device. In some embodiments, the first cannula device may emit a light of a first color corresponding to a size of the first cannula device and the second cannula device may emit a light of a second color corresponding to a size of the second cannula device. In some embodiments, the second color may be different from the first color.

Persons of ordinary skill in the art will appreciate that the implementations encompassed by the present disclosure are not limited to the particular exemplary implementations described above. In that regard, although illustrative implementations have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A set of cannula devices for a vitreo-retinal surgical procedure in an eye, comprising:
   a first cannula device comprising a first tube configured for entry of a first surgical instrument through the first tube and into the eye, and a first hub at a proximal end of the first tube;
   a second cannula device, physically distinct from the first cannula device, comprising a second tube configured for entry of a second surgical instrument through the second tube and into the eye, and a second hub at a proximal end of the second tube,
   wherein the first tube has a different gauge size from the second tube;
   wherein the first hub has a material that is self-illuminating, configured to emit a light, and a first sealing element comprising a first color corresponding to the gauge size of the first tube; and
   wherein the second hub has a material that is self-illuminating, configured to emit a light, and a second sealing element comprising a second color corresponding to the gauge size of the second tube, wherein the second color is different from the first color.

2. The set of cannula devices of claim 1, wherein the first cannula device comprises phosphors that make the cannula device self-illuminating.

3. The set of cannula devices of claim 2, wherein the phosphors comprise zinc sulfide or strontium aluminate.

4. The set of cannula devices of claim 2, wherein the phosphors are incorporated in the first hub.

5. The set of cannula devices of claim 2, wherein the first sealing element is configured to seal a passage through the first tube when the first sealing element is in a relaxed condition, wherein the phosphors are incorporated in the first sealing element.

6. The set of cannula devices of claim 1, wherein the first sealing element is purple to indicate the first tube gauge size is 27 gauge, blue to indicate the first tube gauge size is 25 gauge, or orange to indicate the first tube gauge size is 23 gauge.

7. The set of cannula devices of claim 1, wherein the first hub is coupled to the first sealing element and wherein the first hub is configured to snap onto the first cannula device.

8. A cannula device for a vitreo-retinal surgical procedure in an eye, comprising:
   a tube configured for entry of a surgical instrument through the tube and into the eye,
   a hub at a proximal end of the tube, wherein the hub acts as a stop limiting advancement of the tube into the eye to prevent the tube from completely entering the eye; and
   a sealing element configured to seal a passage through the tube when the sealing element is in a relaxed condition, wherein the sealing element comprises one or more slits to allow passage of the surgical instrument, wherein the sealing element is color-coded to indicate a gauge size of the tube;
   wherein the hub comprises a self-illuminating material and circumscribes the color-coded sealing element, which does not contain a self-illuminating material, such that the hub forms an illuminated circular target around the one or more slits in the sealing element to act as a target for insertion of the surgical instrument into the one or more slits during the surgical procedure.

9. The cannula device of claim 8, wherein the hub's self-illuminating material comprises phosphors that make the hub self-illuminating.

10. The cannula device of claim 9, wherein the phosphors, when in an activated condition, emit a color-coded light corresponding to a size of the tube.

11. The cannula device of claim 8, wherein the phosphors comprise zinc sulfide.

12. The cannula device of claim 8, wherein the phosphors comprise strontium aluminate.

13. The cannula device of claim 8, wherein the sealing element is purple to indicate the tube gauge size is 27 gauge, blue to indicate the tube gauge size is 25 gauge, or orange to indicate the tube gauge size is 23 gauge.

14. The cannula device of claim 8, wherein the hub is coupled to the sealing element and wherein the hub is configured to snap onto the cannula device.

\* \* \* \* \*